(12) United States Patent
Schiffmann

(10) Patent No.: US 6,986,758 B2
(45) Date of Patent: Jan. 17, 2006

(54) DEVICE FOR ADMINISTERING AN INJECTABLE PRODUCT IN DOSES

(75) Inventor: Frank Schiffmann, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/738,073

(22) Filed: Dec. 17, 2003

(65) Prior Publication Data

US 2004/0133163 A1    Jul. 8, 2004

Related U.S. Application Data

(63) Continuation of application No. PCT/CH02/00312, filed on Jun. 12, 2003.

(30) Foreign Application Priority Data

Jun. 20, 2001    (DE) .................................. 101 29 585

(51) Int. Cl.
*A61M 37/00* (2006.01)
*A61M 5/178* (2006.01)
*A61M 5/30* (2006.01)

(52) U.S. Cl. .................. 604/131; 604/207; 604/70; 604/218

(58) Field of Classification Search ................ 604/131, 604/207–217, 70–72, 191, 6, 186, 140–181; 141/329

See application file for complete search history.

(56) References Cited

U.S. PATENT DOCUMENTS

| 5,300,041 | A | 4/1994 | Smedley et al. |
| 6,090,070 | A | 7/2000 | Hager et al. |
| 6,689,101 | B2 * | 2/2004 | Hjertman et al. ........... 604/131 |
| 6,752,781 | B2 * | 6/2004 | Landau et al. ................ 604/70 |
| 2001/0004681 | A1 * | 6/2001 | Landau ........................ 604/70 |
| 2002/0007142 | A1 | 1/2002 | Fridholm et al. |
| 2003/0078536 | A1 * | 4/2003 | Alexandre et al. ............ 604/70 |

FOREIGN PATENT DOCUMENTS

WO    WO 01/89613    11/2001

* cited by examiner

*Primary Examiner*—Nicholas D. Lucchesi
*Assistant Examiner*—Roz Maiorino
(74) *Attorney, Agent, or Firm*—Dorsey & Whitney LLP

(57) ABSTRACT

A device for administering an injectable product in doses including a dosage reservoir from which a product dosage is administered, a storage reservoir for storing the product, a transfer conveyor for conveying the product dosage from the storage reservoir into the dosage reservoir, an evacuator for evacuating the dosage reservoir, and a dosing and activating mechanism for performing a dosing movement for selecting the product dosage, a conveying movement for activating the transfer conveyor and an evacuating movement for activating the evacuator.

22 Claims, 3 Drawing Sheets

DEVICE FOR ADMINISTERING AN INJECTABLE PRODUCT IN DOSES

CROSS-REFERENCE TO RELATED APPLICATION(S)

This application is a continuation of International Application No. PCT/CH02/00312, filed on Jun. 12, 2003, which claims priority to German Patent Application No. 10129585.5, filed on Jun. 20, 2001, the contents of both are herein incorporated in their entirety by reference.

BACKGROUND

The invention relates to a device for administering an injectable product, the device having at least two reservoirs for holding the product. The product is delivered and administered from a first reservoir, the dosage reservoir. A second reservoir serves as a storage reservoir for the product. For administering, the product is conveyed from the storage reservoir into the dosage reservoir. The device is suited for delivering a product that is a medically or cosmetically active fluid, for example, a liquid with at least one medically or cosmetically active substance dissolved or suspended therein. Specific examples of suitable products for administration by the device include growth hormones and insulin. The device may be used for self-administration of the product, that is, the device may be used by a user who administers the product him/herself.

Transferring the product from the storage reservoir to the dosage reservoir requires evacuation of the product form the storage reservoir and, more specifically, evacuation of the correct dosage of the product from the storage reservoir to the dosage reservoir. Correct dosing can present a problem in self-administration of a product. It is desirable that a device for self-administration of a product by simple and safe to handle.

SUMMARY

The present invention provides a device for administering an injectable product, the device having two reservoirs, a first reservoir, the dosage reservoir, for receiving and administering a dosage of the product and a second reservoir, the storage reservoir, for storing the product. The product dosage to be administered is selected and transferred from the storage reservoir into the dosage reservoir. The dosage reservoir is then evacuated during administration with simple handling.

In one embodiment, the present invention comprises a device for administering an injectable product in doses, the device comprising a dosage reservoir from which a product dosage is administered, a storage reservoir for storing the product, a transfer conveyor for conveying the product dosage from the storage reservoir into the dosage reservoir, an evacuating means for evacuating the dosage reservoir, and a dosing and activating means, connected to a casing, by which a dosing movement for selecting the product dosage, a conveying movement for activating the transfer conveyor and an evacuating movement for activating the evacuating means can be performed relative to the casing.

The device of the present invention includes a storage reservoir and a dosage reservoir for the product. The storage reservoir stores a supply of the product. The dosage reservoir receives from the storage reservoir a selected dosage of the product to be administered. The dosage reservoir is formed by or accommodated by a casing. A first conveyor, or transfer conveyor, conveys a selected product dosage from the storage reservoir into the dosage reservoir. A second conveyor, or administration conveyor, conveys the product dosage from the dosage reservoir during administration of the product. Each of the first and second conveyors may be formed of any suitable device, such as a pump. For example, the conveyors may each be a piston in the respective reservoir and which may be shifted toward a reservoir outlet in that reservoir. If both conveyors are pistons, and thus if the product is conveyed from both reservoirs by pistons, the reservoirs may be formed and arranged such that the pistons are moved in the same direction during their conveying movements. Further, the reservoirs and conveyors may be configured such that the movement axes of the pistons are flush.

The device of the present invention further includes an evacuating device for evacuating the dosage reservoir, and a dosing and activating means. The dosing and activating means controls the selection of the product dosage to be administered and activates the first and second conveyors and the evacuating device. The dosing and activating means is connected to the casing such that the product dosage is selected by a dosing movement relative to the casing, the transfer conveyor is activated by a conveying movement relative to the casing, and the evacuating means is activated by an evacuating movement relative to the casing. The movements of the dosing and activating means can be rotational or translational forms of movement or a combination of rotational and translational forms of movement. Each of the dosing movement, conveying movement, and evacuating movement may be different movements. The conveying movement and the evacuating movement are preferably translational movements. These two movements may be a single translational movement, in which case the conveying movement forms a first part of the translational movement and the evacuating movement forms a second part of the translational movement. Although the dosing movement may also be a translational movement, the dosing movement is preferably a rotational movement. Such a rotational dosing movement may be performed about an axis along which the conveying movement and/or the evacuating movement occurs. If the second conveyor is a piston, the translational evacuating movement of the dosing and activating means occurs in the same direction as the piston movement. Further, the axes of the piston movement and the evacuating movement may be flush. Thus, if the product dosage is conveyed out of the storage reservoir by the movement of a piston accommodated therein, a translational conveying movement of the dosing and activating means preferably points in the same direction as the piston movement. Further, the movement axis of the piston of the storage reservoir and the axis of the translational conveying movement of the dosing and activating means may be flush.

The invention may be configured as a pressure injector, for example, a needle-free pressure injector. The invention is not, however, limited to needle-free pressure injectors, but can be used in all injection apparatus or in infusion apparatus wherein a selected product dosage is transferred, with subsequent evacuation.

In accordance with the invention, the device further includes at least one stopper element mounted movably on or in the casing, and at least one slaving means mounted movably on or in the casing. The stopper element is coupled to the dosing and activating means such that the dosing movement of the dosing and activating means generates a positioning movement of the stopper element into a stopper position for the transfer conveyor. In its stopper position, the stopper element limits the conveying movement of the transfer conveyor. The slaving means is coupled to the dosing and activating means such that the dosing movement of the dosing and activating means generates a positioning movement of the slaving means into a stopper position. The slaving means is further coupled to the dosing and activating means such that the evacuating movement of the dosing and activating means generates an evacuating movement of the slaving means out of its stopper position. The slaving means is coupled to the evacuating means such that it slaves the evacuating means during its evacuating movement. The stopper position of the slaving means is preferably a stopper position for the dosing and activating means which at the end of its conveying movement comes to rest against the slaving means and triggers its evacuating movement or, more preferably, slaves the slaving means during its own evacuating movement.

As the dosing movement of the dosing and activating means positions both a stopper element for the transfer conveyor and a slaving means for the evacuating means, each in stopper positions, both the transfer conveyor and the evacuating means are clearly defined. Conveying by the transfer conveyor into the dosage reservoir is limited by a stopper and evacuating is initiated by a stopper. This enables conveying, for the purpose of transferring from the storage reservoir, and evacuating from the dosage reservoir to be simply but precisely adjusted to each other. The processes of conveying and evacuating are dependent on each other. Specifically, given a constant volume of the dosage reservoir, once a product dosage has been poured or placed in the reservoir which does not take up the entire volume of the dosage reservoir, a residual volume remains that needs to be evacuated. The size of the residual volume depends on the product dosage placed in or contained in the reservoir.

In a preferred embodiment, the stopper element and the casing are connected to each other by a first cam joint, preferably a screw joint. Positioning the slaving means is done by a movement along a rotational axis, preferably a screw axis, of the first cam joint. Irrespective of the coupling between the stopper element and the casing, it is also advantageous if the slaving means and the evacuating means are connected to each other by a second cam joint, preferably a screw joint, and positioning the slaving means is done by a movement along a rotational axis, preferably a screw axis, of the second cam joint. Positioning with the aid of two cam joints allows the two positioning movements to be simply adjusted. The dosing and activating means assumes the function of a coupling member, preferably either by engaging directly with both the stopper element and the slaving means or by only engaging directly with one of these elements and engaging with the other one via at least one intermediate member.

BRIEF DESCRIPTION OF THE DRAWINGS

An exemplary embodiment of the invention will now be shown in and explained with reference to the following figures.

DETAILED DESCRIPTION

Figure 1:
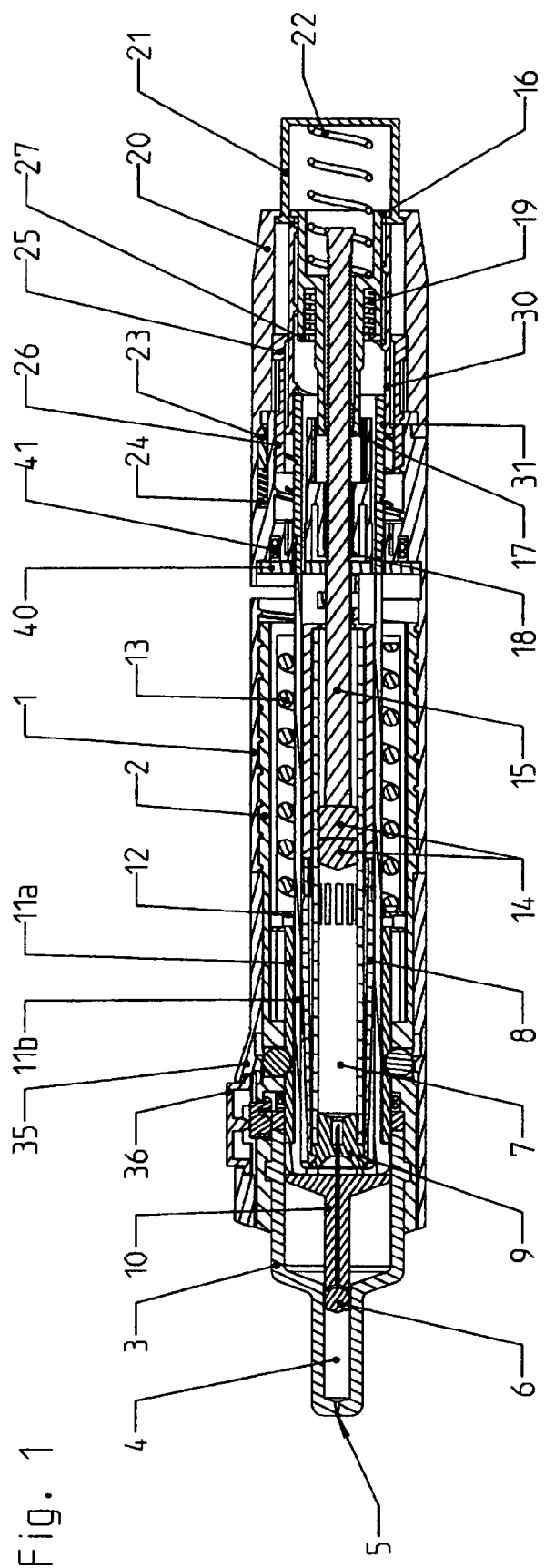
FIG. 1 is a perspective view of a device in accordance with the invention, in a longitudinal section.

FIG. 1 shows a longitudinal section of a device for administering an injectable product which is formed, for example, as a pressure injector for a needle-free injection. The longitudinal section includes the central longitudinal axis of the device.

The device as shown comprises a three-part casing including a rear casing part 1, a middle casing part 2 and a front casing part 3. The casing parts 1, 2 and 3 are sleeve-shaped. As shown, the middle casing part 2 is screwed into the rear casing part 1 and protrudes beyond a front end of the rear casing part 1. The front casing part 3 is detachably connected to the middle casing part 2 in a positive lock and protrudes beyond a front end of the middle casing part 2. The front casing part 3 forms, at a front end, a dosage reservoir 4. The three casing parts may be connected in any suitable manner, and the casing may be formed of more or less than three parts.

The dosage reservoir, or pressure chamber, 4 includes a dosage reservoir outlet 5 at its foremost free end. The dosage reservoir 4 may be formed as a pressure chamber from which a product dosage stored therein is delivered at high pressure through the dosage reservoir outlet 5. During delivery, the conditions in the dosage reservoir 4 and the dosage reservoir outlet 5 are such that a directed product stream is expelled through the dosage reservoir outlet 5 at a sufficiently high pressure for the product stream to enter a tissue at an injection point to a desired depth, for the purpose of injection, and upon reaching the desired depth of penetration to be distributed laterally. Of course, if the device of the invention is used with a needle, and thus not as a pressure injector, the product stream need not be expelled at the high pressure required for pressure injection.

The product dosage is delivered or expelled from the dosage reservoir 4 by an administration conveyor such as a piston 6 in the dosage reservoir 4. The piston 6 is positioned such that it may be linearly shifted, in an expelling movement, towards the dosage reservoir outlet 5. The expelling movement of the piston 6 is generated by an injection spring 13. Other types of drive for generating the expelling movement, for example gas pressure, may alternately be used. The injection spring 13 is positioned in an annular gap between the middle casing part 2 and a sleeve-shaped evacuating means 11a and is pressurized before an injection is triggered. The injection spring 13 is then supported via its rear end on a collar of the middle casing part 2 protruding radially inwards and presses via its front end against a drive element 11b of a drive means. The drive element 11b comprises a flange 12, projecting radially outwards, at its rear end against which the injection spring 13 presses. The evacuating means 11a and the drive element 11b are positioned in the middle casing part 2 such that they may be linearly shifted towards the dosage reservoir outlet 5. The evacuating means 11a and the drive element 11b may be axially shifted relative not only to the casing but also to each other. As shown, the sleeve-shaped drive element 11b surrounds the evacuating means 11a concentrically. In a rear position shown in FIG. 1, in which the injection spring 13 is tensed, the drive element 11b is secured against axially shifting towards the dosage reservoir outlet 5.

A piston rod 10 arranged between the piston 6 and the evacuating means 11a transfers the translational movement of the evacuating means 11a onto the piston 6. The piston rod 10 comprises a rear, plinth-like region which the evacuating means 11a presses against during its expelling movement, and a front region which protrudes from the plinth-like region towards the piston 6. The piston rod 10 presses against the piston 6 via its front free end. At least one connecting channel, through which the product may be conveyed, extends through the piston rod 10. A connecting needle is inserted in the at least one connecting channel, protrudes backwards beyond the piston rod 10, and forms a fluid connection to a storage reservoir 7.

The storage reservoir 7 is formed by an ampoule which is accommodated within the rear and middle casing parts 1 and 2 by an ampoule holder 8. The ampoule holder 8 is sleeve-shaped and supported via its rear end on an unlocking element 40 inserted in the rear casing part 1. Holding elements protrude radially inwards from the middle casing part 2 through cavities in the evacuating means 11a which suitably fix the ampoule holder 8 in a positive and/or frictional lock. The ampoule 7 is inserted into the ampoule holder 8 up to a rear collar of the ampoule holder 8 protruding inwards. A membrane 9 seals the ampoule 7 imperviously to the front. The sleeve arrangement consisting of the ampoule 7 and the ampoule holder 8 is accommodated in the sleeve-shaped evacuating means 11a and presses via the front end of the ampoule holder 8 against a front collar of the evacuating means 11a protruding inwards, as soon as the device has been assembled. In this way, the ampoule holder 8 and the ampoule 7 are defined and held immovably relative to the casing parts 1 and 2.

The ampoule 7 may be a twin-chamber ampoule. Alternately, a single ampoule or other ampoule configuration may be used. While the ampoule 7 is stored, a powdery agent is provided in a front section of the ampoule 7. A liquid is provided in a rear section of the ampoule 7. Two pistons 14 are positioned in the ampoule such that they may be shifted towards the membrane 9. While the ampoule 7 is stored, the front piston 14 separates the liquid from the powdery agent, and the rear piston 14 seals off the section of the ampoule 7 filled with the liquid, the liquid being enclosed between the two pistons 14. To prepare the product for administering, the liquid and the powdery agent are mixed, by shifting the rear piston 14 towards the membrane 9. The incompressibility of the liquid causes the front piston 14 to be shifted together with the rear piston 14. This shift releases a division between the rear ampoule section and the front ampoule section. If the rear piston 14 is advanced further, the liquid from the rear ampoule section passes through the division into the front ampoule section and mixes with the powdery agent. Once the rear piston 14, in the course of this mixing movement, pushes against the front piston 14, the liquid is displaced from the rear ampoule section and the mixing process is complete. The injectable product, the agent and liquid mixture, is situated in the front ampoule section and can be displaced from the ampoule 7 by advancing the two pistons 14. The mixing process described is automatically performed when the device is assembled, i.e. when the rear and middle casing parts 1 and 2 are screwed together.

For administering, a selected product dosage is transferred from the ampoule 7 into the dosage reservoir 4. In the embodiment shown, the product dosage can be selected or set by a user. The product passes through the connecting needle and the connecting channel formed in the piston rod 10 to the front free end of the piston rod 10 opposite the rear side of the piston 6. Between the rear side of the piston 6 and the front free end of the piston rod 10, the product flows radially outwards and enters groove channels formed in the region of the inner surface area of the front casing part 3 which surrounds the piston 6 in its initial position before an injection, shown in FIG. 1. The groove channels lead past the piston 6 into the dosage reservoir 4 and thus establish a connection between the connecting channel of the piston rod 10 and the dosage reservoir 4.

As the dosage reservoir, or pressure chamber, 4 receives a product dosage selected by the user, thus allowing doses of different sizes, a residual volume filled with air or another compressible gas is formed in the dosage reservoir 4. The residual volume is formed after each transferring process, the size of the volume depending on the product dosage. Generally speaking, the larger the product dosage, the smaller the residual volume, and vice versa.

A dosing and activating means, comprising a dosing member 20 and an activating member 21 controls the selection of the product dosage to be transferred and administered. It also activates a transfer conveyor comprising the front and rear pistons 14, for conveying the product dosage from the storage reservoir, or ampoule, 7 into the dosage reservoir, or pressure chamber, 4, and in cooperation with the evacuating means 11a evacuates the dosage reservoir 4 after the transfer. The dosing and activating means 20, 21 is coupled to a control mechanism such that the control mechanism is positioned by a dosing movement of the dosing and activating means 20, 21. Thus, when the dosing and activating means 20, 21 is activated, transferring and evacuating are performed in a manner adjusted to one another.

The dosing member 20 is provided for performing the dosing movement. It is rotatably connected to the rear casing part 1, such that the dosing movement is a rotational movement. As shown, it is a rotational movement about the central longitudinal axis of the device, which is identical to the movement axes of the pistons 6 and 14. The product is dosed in discrete increments in cooperation with a grid pin 23. The grid pin 23 is positioned in a cylindrical, axial hollow space, open to the rear, of the rear casing part 1 and is pressed against an axial facing area of the dosing member 20 by the influence of a pressure spring 24, likewise accommodated therein. Recesses are formed in the axial facing area of the dosing member 20, in accordance with the grid pitch, for receiving the grid pin 23.

The activating member 21 is connected to the dosing member 20 such that it can be shifted back and forth along the rotational axis of the dosing member 20. The activating member 21 protrudes backwards out of the sleeve-shaped dosing member 20. The activating member 21 is cup-shaped with a base at its rear end and a collar edge, the collar edge protruding radially inwards and radially outwards beyond the walls of the cup, at its front end.

The dosing member 20 engages with a sleeve-shaped stopper element 25. The engagement is such that a rotational movement of the stopper element 25 about the rotational axis of the dosing member 20 is prevented, but a translational movement of the stopper element 25 along the rotational axis of the dosing member 20 is possible. As shown, the translational movement of the stopper element 25 is a linear shift. The stopper element 25 is inserted into the dosing member 20 via its rear region and interlocks with blind grooves of the dosing member 20, forming a rotational block. A front region of the stopper element 25 forms a screw joint 26 with the rear casing part 1. Through these two couplings, with the dosing member 20 and with the rear casing part 1, the stopper element 25 can be moved along the rotational axis of the dosing member 20 into a stopper position. Thus, the stopper element 26 may be positioned, by the dosing movement of the dosing member 20 and in accordance with the extent of the dosing movement.

The control mechanism to which the dosing and activating means 20, 21 is coupled further comprises a sleeve-shaped slaving means 30. The slaving means 30 is coupled to the dosing member 20 in such a way that a rotational movement of the slaving means 30 about the rotational axis of the dosing member 20 is prevented, but a translational movement of the slaving means 30 along the rotational axis of the dosing member 20 is possible. As shown, the translational movement of the slaving means 30 is a linear shift. The dosing member 20 and the slaving means 30 are coupled via the stopper element 25, by the slaving means 30 protruding into the sleeve-shaped stopper element 25, forming the rotational block between the stopper element 25 and the slaving means 30, in a positive lock. A front section of the slaving means 30 comprises a screw thread on its inner surface area, the slaving means 30 thereby forming a screw joint 26 with the evacuating means 11a. The coupling between the slaving means 30 and the dosing member 20 and the evacuating means 11a is such that the slaving means 30 is moved along the movement axis of the evacuating means 11a, which, as shown, coincides with the rotational axis of the dosing member 20, into a stopper position. Thus, the slaving means 30 may be positioned, relative to the evacuating means 11a and the activating member 21 by the dosing movement of the dosing member 20.

As already mentioned, the dosing and activating means 20, 21 activates a transfer conveyor for the storage reservoir, the conveying action of the transfer conveyor transferring the selected product dosage from the storage reservoir, or ampoule, 7 into the dosage reservoir, or pressure chamber, 4. The transfer conveyor comprises the front and rear pistons 14, a piston rod 15 and a sleeve-shaped advancing element 16. The piston rod 15 protrudes into the ampoule 7 from behind. When activated, the piston rod 15 presses against the rear piston 14 and advances the rear piston 14 towards the membrane 9. The piston rod 15 is formed in a rear piston rod region. As shown, the piston rod 15 may be formed as a toothed rack having a serrated tooth profile. The advancing element 16 engages with the serrated tooth profile via engaging elements 17, such that when the advancing element 16 moves towards the membrane 9, the piston rod 15 is slaved and for its part presses against the rear piston 14. The engagement of the engaging elements 17 prevents the piston rod 15 from being retracted relative to the advancing element 16. In order to also prevent the piston rod 15 from being retracted relative to the ampoule 7, the rear casing part 1 includes locking elements 18 which prevent such a relative movement by engaging with the serrated tooth profile of the piston rod 15. Other types of connection between an advancing element and a piston rod which are connected rigid against shifting in the advancing direction may also be used. Further, the advancing element and piston rod may be formed as one piece.

In its stopper position, the stopper element 25 acts as a stopper for the advancing element 16. A collar 27 of the stopper element 25 protruding radially inwards at the rear end of the stopper element 25 forms the stopper for the advancing element 16 protruding into the slaving means 30. The slaving means 30 protrudes through the collar 27 of the stopper element 25. The nested arrangement of the dosing member 20, the stopper element 25 and the slaving means 30 reduces the axial length of the device. The axial length is also reduced by the control mechanism to which the dosing and activating means is coupled and the dosing member 20 surrounding the advancing element 16 and, at least before the product is first administered, also the piston rod 15.

The activating member 21 acts on the advancing element 16 via a pressure spring 22. The pressure spring 22 is guided in a cylindrical hollow space of the advancing element 16, open towards the rear, and supported on a base of the hollow space and on the base of the activating member 21. Another elastic restoring element 19, also a pressure spring in the embodiment shown, is arranged between the advancing element 16 and the stopper element 25, such that it is tensed when the advancing element 16 is moved against the stopper element 25, i.e. against the collar 27 of the stopper element 25.

When the dosage reservoir, or pressure chamber, 4 has been filled with the product dosage, and—after it has been filled—evacuated, administering can be triggered by activating a trigger. The trigger includes a triggering sleeve 35 and a triggering element 36. The triggering sleeve 35 is connected to the middle casing part 2 such that it can be shifted. The triggering sleeve 35 can shift towards the dosage reservoir outlet 5 of the dosage reservoir 4 relative to the rear and middle casing parts 1 and 2. The triggering element 36 is fastened to the triggering sleeve 35 and functions as a triggering button. For triggering, two movements must be performed. The triggering sleeve 35 must be advanced relative to the rear, middle, and front casing parts 1, 2 and 3. Further, with the triggering sleeve 35 in its advanced position, the triggering element 36 must be pressed radially inwards. If both movements are performed, then the drive element 11b is unlocked and pushes forward, i.e. towards the dosage reservoir outlet 5, due to the pressure of the injection spring 13. At this moment, the drive element 11b acts as a plunger for the piston rod 10 and the piston 6. In the embodiment shown, the drive element 11b pushes during its advancing movement against a collar of an evacuator 11a which during the evacuating process is already slightly advanced a with the collar abutting the piston rod 10.

The functionality and/or method of use of the device of the present invention is described below on the basis of the sequence of FIGS. 2 to 7. FIGS. 2 to 7 each show only the rear part of the device, including the dosing and activating means 20, 21 and the control mechanism 25, 30. With respect to the front part of the device, reference is made to FIG. 1.

Figure 2:
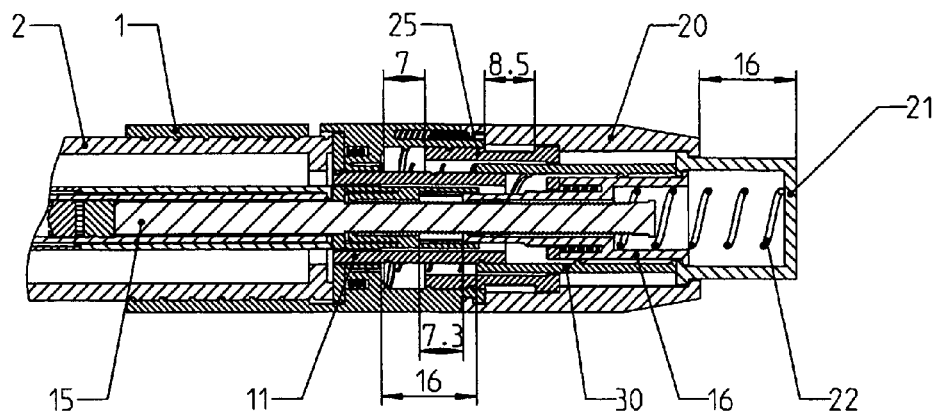
FIG. 2 is a perspective view of a rear part of the device in FIG. 1, in an initial position.

FIG. 2 shows the device in an initial position in which the ampoule 7 is inserted, the middle and rear casing parts 1 and 2 are connected together, the mixing process for producing the product thus performed, and the front casing part 3 fixedly connected to the middle casing part 2 in a positive lock. In the initial position, the device is ready for selecting the product dosage to be transferred from the storage reservoir, or ampoule, 7 into the dosage reservoir, or pressure chamber, 4, for administration. The user sets or selects the product dosage using the dosing member 20. When the dosing movement is performed, the product dosage is indicated to the user optically and by a clicking sound caused by the dosing member 20 cooperating with the grid pin 23. Of course, alternate indicators may be used. Before a first dosing movement is performed, the piston rod 15, the advancing element 16, the stopper element 25, the slaving means 30 and the activating member 21 are situated in their rearmost positions which are each defined by stoppers.

In FIGS. 2 to 7, exemplary maximum adjusting paths of the stopper element 25 and the slaving means 30 are illustrated. The path lengths and measurements provided are for illustrative purposes only and are not intended to be limiting. The maximum adjusting path of the stopper element 25 measures approximately 7 mm and the maximum adjusting path of the slaving means 30 measures approximately 16 mm. This means that, as a result of a dosing movement of the dosing member 20, the stopper element 25 can be advanced by a maximum of approximately 7 mm relative to the rear casing part 1 and in particular relative to the piston rod 15, towards the outlet of the ampoule 7. Similarly, the slaving means 30 can be advanced by a maximum of approximately 16 mm relative to the evacuating means 11a, towards the dosage reservoir outlet 5 from its initial position. The stroke of the activating member 21 is as long as the maximum adjusting path of the slaving means 30; the stroke is correspondingly specified in the embodiment shown as approximately 16 mm. The maximum adjusting paths of the stopper element 25 and the slaving means 30 correspond to one complete rotation of the dosing member 20.

Figure 3:
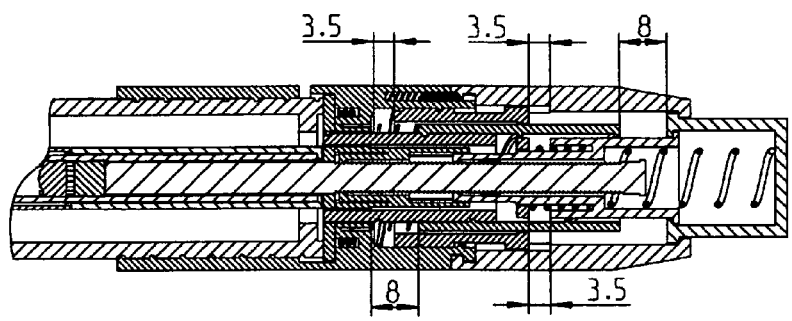
FIG. 3 is a perspective view of the rear part, once a product dosage has been set.

FIG. 3 shows the device once the product dosage has been set. As shown, half of the maximum dosage which can be administered in one injection has been set, i.e. the stopper element 25 has been advanced by approximately 3.5 mm and the slaving means 30 by approximately 8 mm. Correspondingly, the advancing element 16 and together with it the piston rod 15 can be advanced by approximately 3.5 mm and the evacuating means 11a by approximately 8 mm (any of the distances mentioned herein may be initially varied), when transferring the product dosage and evacuating the dosage reservoir, or pressure chamber, 4. From this position, the activating member 21 still in its initial position, presses into the dosing member 20. The shifting movement of the activating member 21 advances the advancing element 16 up to and against the stopper element 25 situated in its initial position. The remaining stroke of the activating member 21 pushes the slaving means 30 out of its stopper position. When slaved by the activating member 21, the slaving means 30, together with the evacuating means 11a, performs an evacuating movement. The evacuating movement ends when the slaving means 30 abuts against a reverse stopper area of the casing part 1.

Figure 4:
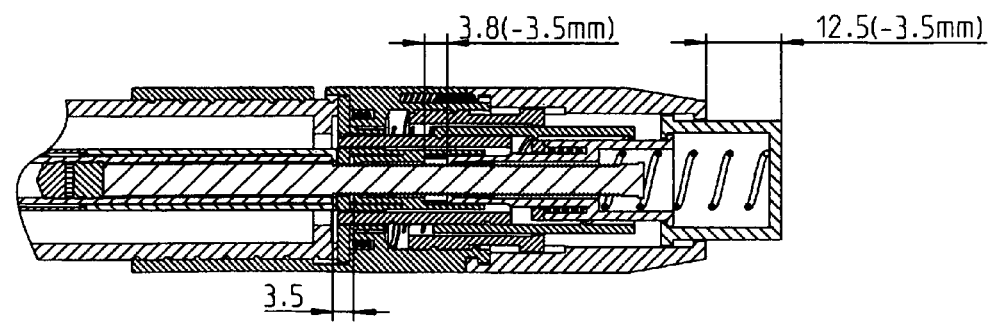
FIG. 4 is a perspective view of the rear part, during a transferring process.

FIG. 4 illustrates the device in an intermediate position at a moment after the product dosage has been transferred and before the dosage reservoir 4 is evacuated. In this intermediate position, the advancing element 16 pushes against the restoring force of the restoring element 19 against the collar 27 of the stopper element 25. As shown, the advancing element 16 and, via the engagement of the engaging elements 17, the piston rod 15 and the front and rear pistons 14 are advanced by approximately 3.5 mm in the course of their conveying movement. The shifting movement of the activating member 21 is transferred onto the advancing element 16 via the pressure spring 22, the pressure spring 22 being sufficiently strong or installed with a such a bias that it is not or is only minimally compressed. When the activating member 21 is inserted further, the activating member 21 comes into contact with the slaving means 30, still in its stopper position, and when inserted further slaves the slaving means 30. Due to the connection, rigid against shifting, between the slaving means 30 and the evacuating means 11a, the evacuating means 11a is also advanced when the activating member 21 is thus inserted further and during this shifting movement presses the piston 6 in the dosage reservoir, or pressure chamber, 4 forwards towards the outlet 5.

The pressure spring 22 is preferably sufficiently strong that the advancing element 16 abuts the stopper element 25 before the slaving means 30 has completely performed its evacuating movement. In one preferred embodiment, the pressure spring 22 is sufficiently strong that the advancing element 16 abuts before the activating member 21 engages with the slaving means 30. In the position illustrated in FIG. 4, a safety distance remains between the activating member 21 and the slaving means 30 when the advancing element 16 abuts the stopper element 25. In the embodiment shown, the safety distance is approximately 1 mm.

Figure 5:
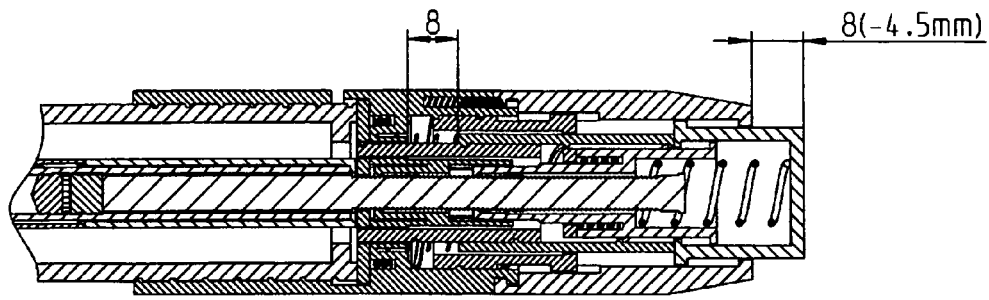
FIG. 5 is a perspective view of the rear part, once transferring is complete and before evacuating.

In the position shown in FIG. 5, the activating member 21 has just traveled the safety distance and has come into stopper contact with the slaving means 30.

Figure 6:
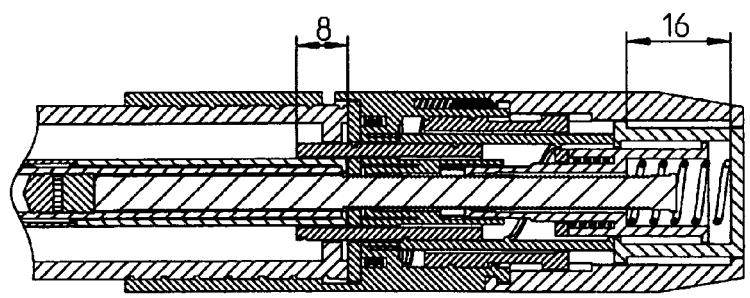
FIG. 6 is a perspective view of the rear part, after evacuating and with the dosing and activating means in a retracted position.

FIG. 6 is the device in a position in which by inserting the activating member 21 further, the slaving means 30 abuts against the rear casing part 1 and the evacuating movement of the slaving means 30 together with the evacuating means 11a has been performed. The evacuating movement is performed against the elastic restoring force of the pressure spring 22. Due to the axial rigidity of the slaving means 30, it is not possible to further insert the activating member 21.

The conveying movement and the evacuating movement of the activating member 21 may be simple linear movement which can be performed continuously in one movement, for example, by pressing the device against a support area such as a support base onto which the device is placed perpendicularly.

The pressure is absorbed by the activating member 21. The restoring forces of the restoring elements 19 and 22 causes the advancing element 16 and the activating member 21 to return to their initial positions relative to the ampoule 7 and the piston rod 15. Due to the engagement of the locking elements 18 in the axial position, the piston rod 15 is held, i.e. the piston rod 15 is not slaved during the reverse movement of the advancing element 16. In this position, the device is ready for administering the product dosage.

To administer the product dosage, the device is held against the tissue, for example human skin, via its foremost end, i.e. the dosage reservoir outlet 5. If the triggering sleeve 35 has to be advanced relative to the rear and middle casing parts 1 and 2 against the force of an elastic restoring element to trigger the injection, the device is pressed against the tissue with an application pressure which may be pre-set by the restoring element. In this position, the triggering element 36 is pressed. This releases the drive element 11b to axially shift. The spring force of the injection spring 13 causes the drive element 11b to push against the evacuating means 11a, the evacuating means 11a having been advanced due to the evacuating movement. The drive element 11b thus presses against the piston rod 10. The drive element 11b pushes against the evacuating means 11a and the piston rod 10 abruptly with kinetic energy and then advances both further due to the spring force of the injection spring 13. At the moment of impact, the spring force and the kinetic energy of the already accelerated drive element 11b act on the piston rod 10. This impacting and advancing force causes the piston rod 10 to shoot abruptly forwards and pushes the piston 6 towards the dosage reservoir outlet 5 at approximately the same speed. This delivers or expels the product dosage at high pressure, in particular at a high initial pressure which decreases to a lower value in the course of the injection.

Figure 7:
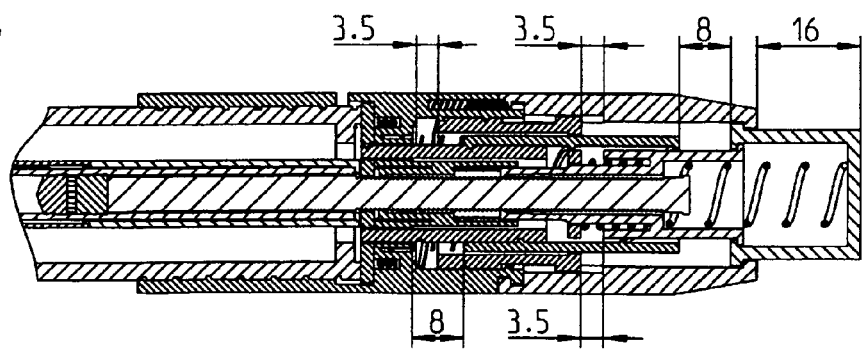
FIG. 7 is a perspective view of the rear part, after evacuating and with the dosing and activating means back in an extended position.

Once the product dosage has been administered, the front casing part 3 is detached from the middle casing part 2, and the evacuating means 11a and the drive element 11b are moved back again, against the force of the injection spring 13, to the position shown in FIG. 1 and FIG. 2. Another product dosage may then be selected and administered from the ampoule 7 which is not yet empty. FIG. 7 shows the device in this position. The drive element 11b may also push directly against the piston rod 10. If, however, the drive element 11b pushes directly in the axial direction against the evacuating means 11a, the evacuating means 11a and the drive element 11b are smoothly moved jointly back to the position shown in FIG. 7.

The device may be reloaded, i.e. once emptied, the ampoule 7 forming the storage reservoir can be exchanged for a new ampoule 7. To exchange the ampoule 7, the rear and middle casing parts 1 and 2 are moved apart and the evacuating means 11a is removed from the rear casing part 1. The ampoule holder 8 together with the old ampoule 7 is then removed from the back of the evacuating means 11a and the new ampoule 7 is inserted into the ampoule holder 8. Removing the evacuating means 11a releases the disc-shaped unlocking element 40 which rises from the rear casing part 1 due to the pressure of the restoring element 41 or number of restoring elements 41. In its raised position, the unlocking element 40 can be rotated relative to the rear casing part 1 about the movement axis of the piston rod 15. When rotated, the unlocking element 40 slaves the piston rod 15, such that the piston rod 15 disengages from its toothed engagement with the advancing element 16 and the locking elements 18. It can then be retracted relative to the rear casing part 1, into the initial position shown in FIGS. 1 and 2. In its rotated position, the unlocking element 40 cannot be pressed into its fitting shown in FIG. 1, against the rear casing part 1, but exhibits a defined distance from its fitting position. The distance is chosen such that it just corresponds to the stroke of the rear piston 14 for the mixing process to be performed when using twin-chamber ampoules 7.

After a new ampoule 7 has been inserted into the ampoule holder 8 and the ampoule holder 8 together with the new ampoule 7 has been inserted into the evacuating means 11a, the rear and middle casing parts 1 and 2 are screwed back together. The piston rod 15 is then situated in its initial position (FIGS. 1 and 2). Because, in its rotated position, the unlocking element 40 exhibits the described, pre-set distance from an opposite base area of the rear casing part 1, the rear piston 14 is advanced by the pressing piston rod 15 when the rear and middle casing parts 1 and 2 are screwed together, and the liquid and the powdery agent are mixed together. Once a prescribed mixing period has been observed, the unlocking element 40 is rotated back, without the piston rod 15 which is already engaged in toothed engagement with the advancing element 16 and the locking elements 18. Once rotated back, the unlocking element 40 is moved back to its initial position shown, i.e. to its fitting position, against the restoring element or elements 41, for example by screwing the two casing parts 1 and 2 further together, up to the initial position shown in FIG. 1.

The front casing part 3, or a new casing part 3 if desired, is then fixedly connected to the middle casing part 2, in a positive lock. As this connection is established, the connecting needle attached to the piston rod 10 punctures the membrane 9, establishing the fluid connection between the dosage reservoir, or pressure chamber, 4 and the storage reservoir, or ampoule, 7. The device then takes up the initial position shown in FIGS. 1 and 2 again.

In the foregoing description, embodiments of the present invention, including preferred embodiments, have been presented for the purpose of illustration and description. The descriptions are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for administering an injectable product in doses, the device comprising:
   a) a casing;
   b) a dosage reservoir, formed or accommodated by the casing, from which a product dosage is administered;
   c) a storage reservoir for storing the product;
   d) a transfer conveyor for conveying the product dosage from the storage reservoir into the dosage reservoir;
   e) an evacuating means for evacuating the dosage reservoir;
   f) a dosing and activating means, connected to the casing, by which a dosing movement for selecting the product dosage, a conveying movement for activating the transfer conveyor and an evacuating movement for activating the evacuating means can be performed relative to the casing;
   g) a stopper element, mounted movably to the casing, which is coupled to the dosing and activating means such that the dosing movement of the dosing and activating means positions the stopper element into a stopper position for the transfer conveyor;
   h) and a slaving means, mounted movably to the casing, which is coupled to the dosing and activating means such that the dosing movement of the dosing and activating means positions the slaving means into a stopper position and the evacuating movement of the dosing and activating means generates an evacuating movement of the slaving means out of its stopper position;
   i) wherein the slaving means slaves the evacuating means during its evacuating movement, thus evacuating the dosage reservoir.

2. The device of claim 1, wherein the stopper element and the casing are connected to one another by a first cam joint and positioning the stopper element is done by a movement along a rotational axis of the first cam joint.

3. The device of claim 2, wherein the conveying movement of the dosing and activating means occurs in the direction of the rotational axis of the first cam joint.

4. The device of claim 2, wherein the dosing and activating means for performing the dosing movement can be rotated about the rotational axis of the first cam joint relative to the casing and slaves the stopper element during its dosing movement.

5. The device of claim 1, wherein the slaving means and the evacuating means are connected to each other by a second cam joint and positioning the slaving means is a movement along a rotational axis of said second cam joint.

6. The device of claim 5, wherein the evacuating movement of the slaving means occurs in the direction of the rotational axis of the second cam joint.

7. The device of claim 5, wherein the evacuating movement of the dosing and activating means occurs in the direction of the rotational axis of the second cam joint.

8. The device of claim 5, wherein the dosing and activating means for performing the dosing movement can be rotated about the rotational axis of the second cam joint relative to the casing and slaves the slaving means during its dosing movement.

9. The device of claim 5, wherein:
the stopper element and the casing are connected to one another by a first cam joint and positioning the stopper element is done by a movement along a rotational axis of the first cam joint;
a cam member of the first cam joint exhibits a first gradient with respect to the rotational axis of the first cam joint and a cam member of the second cam joint exhibits a second gradient with respect to the rotational axis of the second cam joint;
and said first gradient and said second gradient are proportional to each other such that a shifting path length traveled by a piston accommodated in the dosage reservoir, for evacuating the dosage reservoir and administering the product dosage, is constant even for different product dosages.

10. The device of claim 1, wherein the stopper element and the slaving means are movably mounted relative to the casing and relative to each other along an axis.

11. The device of claim 1, wherein the dosing and activating means and the stopper element and the slaving means are configured as sleeve bodies arranged overlapping each other.

12. The device of claim 1, wherein the dosing and activating means and an advancing element, which acts directly or via a piston rod on a piston accommodated in the storage reservoir, are movably mounted along an axis.

13. The device of claim 1, wherein the stopper element is coupled to the dosing and activating means, secured against rotation but such that it can be shifted.

14. The device of claim 1, wherein the slaving means is coupled to the dosing and activating means, secured against rotation but such that it can be shifted.

15. The device of claim 1, wherein:
a piston is accommodated in the storage reservoir and is advanced towards an outlet of the storage reservoir by a piston rod, for conveying the product;
and the dosing and activating means slaves the piston rod during a conveying movement in the advancing direction of the piston rod, until the piston rod or an advancing element connected fixedly or secured against shifting to the piston rod abuts the stopper element which is situated in its stopper position.

16. The device of claim 1, wherein an elastically acting restoring element, arranged between the dosing and activating means and the transfer conveyor, transfers the conveying movement of the dosing and activating means onto the transfer conveyor.

17. The device of claim 1, wherein the evacuating movement of the dosing and activating means is performed against the force of an elastically acting restoring element arranged between the dosing and activating means and the transfer conveyor.

18. The device of claim 1, wherein a piston is accommodated in the dosage reservoir for delivering the product and the evacuating means shifts the piston towards an outlet of the dosage reservoir during the evacuating movement.

19. The device of claim 1, wherein the transfer conveyor comprises a piston which is accommodated in the storage reservoir and is shifted towards an outlet of the storage reservoir by the conveying movement of the dosing and activating means.

20. A device for administering an injectable product in doses, the device comprising:
a) a dosage reservoir from which a product dosage is administered;
b) a storage reservoir for storing the product;
c) a transfer conveyor for conveying the product dosage from the storage reservoir into the dosage reservoir;
d) an evacuating means for evacuating the dosage reservoir;
e) a dosing and activating means, connected to a casing, for performing a dosing movement for selecting the product dosage, a conveying movement for activating the transfer conveyor and an evacuating movement for activating the evacuating means; and
f) a stopper element coupled to the dosing and activating means such that the dosing movement of the dosing and activating means positions the stopper element into a stopper position for the transfer conveyor.

21. The device of claim 20, further including a slaving means coupled to the dosing and activating means such that the dosing movement of the dosing and activating means positions the slaving means into a stopper position and the evacuating movement of the dosing and activating means generates an evacuating movement of the slaving means out of its stopper position.

22. The device of claim 21, wherein the slaving means slaves the evacuating means during its evacuating movement, thus evacuating the dosage reservoir.

* * * * *

UNITED STATES PATENT AND TRADEMARK OFFICE
CERTIFICATE OF CORRECTION

PATENT NO. : 6,986,758 B2  
APPLICATION NO. : 10/738073  
DATED : January 17, 2006  
INVENTOR(S) : Frank Schiffmann Page 1 of 1

It is certified that error appears in the above-identified patent and that said Letters Patent is hereby corrected as shown below:

Title page,
Item [63], Related U.S. Application Data, delete "Continuation of application no. PCT/CH02/00312, filed on Jun. 12, 2003" and insert -- Continuation of application no. PCT/CH02/00312, filed on Jun. 12, 2002 --.

Column 1,
Line 31, delete "product form the" and insert -- product from --.
Line 36, delete "product by simple" and insert -- product be simple --.

Signed and Sealed this

Twentieth Day of June, 2006

JON W. DUDAS
*Director of the United States Patent and Trademark Office*